United States Patent
Obradovic et al.

(10) Patent No.: US 10,893,930 B2
(45) Date of Patent: Jan. 19, 2021

(54) STENT GRAFT

(71) Applicant: Bentley InnoMed GmbH, Hechingen (DE)

(72) Inventors: Milisav Obradovic, Lorrach (DE); Rainer Bregulla, Balingen (DE)

(73) Assignee: Bentley InnoMed GmbH, Hechingen (DE)

( * ) Notice: Subject to any disclaimer, the term of this patent is extended or adjusted under 35 U.S.C. 154(b) by 0 days.

(21) Appl. No.: 15/760,538

(22) PCT Filed: Sep. 20, 2016

(86) PCT No.: PCT/EP2016/072212
§ 371 (c)(1),
(2) Date: Mar. 15, 2018

(87) PCT Pub. No.: WO2017/050710
PCT Pub. Date: Mar. 30, 2017

(65) Prior Publication Data
US 2018/0256313 A1   Sep. 13, 2018

(30) Foreign Application Priority Data
Sep. 21, 2015 (DE) .................. 10 2015 115 891

(51) Int. Cl.
*A61F 2/07* (2013.01)
*A61F 2/915* (2013.01)
(Continued)

(52) U.S. Cl.
CPC .................. *A61F 2/07* (2013.01); *A61F 2/89* (2013.01); *A61F 2/915* (2013.01); *A61F 2/852* (2013.01);
(Continued)

(58) Field of Classification Search
CPC ........ A61F 2/07–2002/075; A61F 2/89; A61F 2210/0014; A61F 2210/0076;
(Continued)

(56) References Cited

U.S. PATENT DOCUMENTS 5,700,285 A * 12/1997 Myers ...................... A61F 2/07
606/198
5,723,004 A *  3/1998 Dereume ................ A61F 2/07
623/1.35

(Continued)

FOREIGN PATENT DOCUMENTS

CN    101945623 A    1/2011
CN    203074935 U    7/2013
(Continued)

OTHER PUBLICATIONS

Translation of DE102015106052.2 by Obradovic, Nicola dated Apr. 21, 2015 (Year: 2015).*
(Continued)

*Primary Examiner* — Paul B Prebilic
(74) *Attorney, Agent, or Firm* — Brooks Kushman P.C.

(57) ABSTRACT

Stent graft consisting of a stent (1) comprising a plurality of ring segments (3, 4) having a meandering configuration arranged side by side and connected with each other by connecting webs (6), and at least one membrane (2) covering the entire outer side of the stent (1), being wrapped inwards around the ends of the stent and fixed between loops of ring segments (4) and connecting webs (6) that join the adjacent ring segments (3, 4) with each other, wherein the membrane (2) is fixed between at least two loops of the second ring segment (4), viewed from the ends of the stent (1), and the connecting webs (6) to the neighboring terminal ring segment (3).

18 Claims, 3 Drawing Sheets

Figure 1:
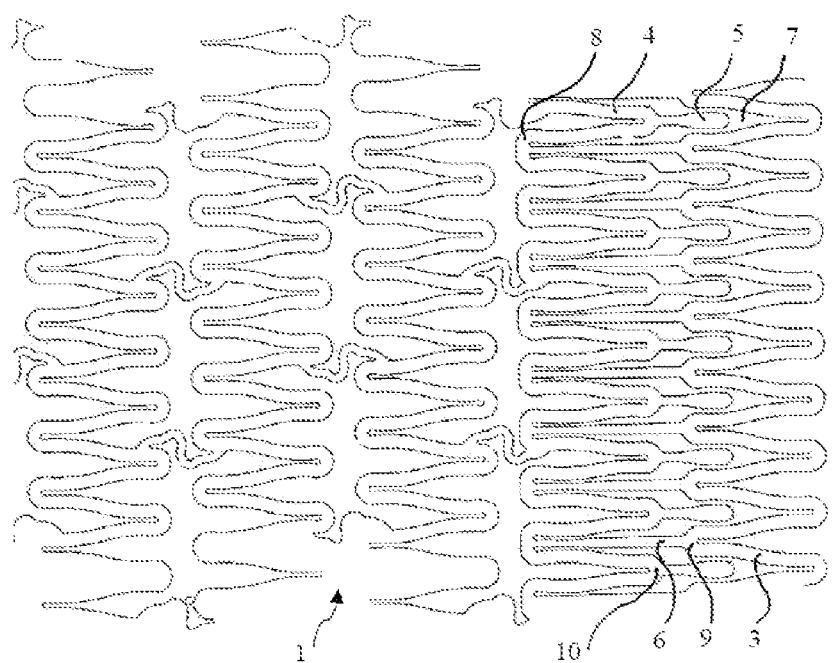

(51) Int. Cl.
*A61F 2/89* (2013.01)
*A61F 2/852* (2013.01)

(52) U.S. Cl.
CPC . *A61F 2002/075* (2013.01); *A61F 2210/0014* (2013.01)

(58) Field of Classification Search
CPC ........ A61F 2220/0075; A61F 2250/001; A61F 2250/0036; A61F 2250/0037
See application file for complete search history.

(56) References Cited

U.S. PATENT DOCUMENTS

| | | | |
|---|---|---|---|
| 6,143,022 A | | 11/2000 | Shull et al. |
| 6,488,701 B1 | | 12/2002 | Nolting et al. |
| 6,699,277 B1 | * | 3/2004 | Freidberg ............... A61F 2/07 623/1.13 |
| 8,888,837 B2 | * | 11/2014 | Obradovi ................ A61F 2/07 623/1.13 |
| 2001/0041928 A1 | * | 11/2001 | Pavcnik .................. A61F 2/07 623/1.13 |
| 2004/0230293 A1 | * | 11/2004 | Yip ........................ A61F 2/915 623/1.16 |
| 2005/0125051 A1 | * | 6/2005 | Eidenschink ............ A61F 2/91 623/1.12 |
| 2005/0228480 A1 | * | 10/2005 | Douglas .................. A61F 2/07 623/1.13 |
| 2013/0013051 A1 | | 1/2013 | Benary |
| 2013/0317595 A1 | * | 11/2013 | Obradovic ............... A61F 2/07 623/1.13 |
| 2015/0105851 A1 | | 4/2015 | Shalev et al. |
| 2018/0116782 A1 | * | 5/2018 | Obradovic ............... A61F 2/07 |
| 2018/0140444 A1 | * | 5/2018 | Neuss ................... A61F 2/2418 |
| 2018/0360631 A1 | * | 12/2018 | Bregulla ................. A61F 2/915 |
| 2019/0262150 A1 | * | 8/2019 | Neuss ..................... A61F 2/915 |

FOREIGN PATENT DOCUMENTS

| | | | | |
|---|---|---|---|---|
| CN | 103402461 A | | 11/2013 | |
| DE | 102015106052.3 | * | 4/2015 | ............... A61F 2/07 |
| EP | 1266635 A2 | | 12/2002 | |
| EP | 2151217 A1 | | 2/2010 | |
| RU | 2010138545 A | | 3/2012 | |
| WO | WO2001/66035 A2 | | 9/2001 | |
| WO | WO2009/035679 A1 | | 3/2009 | |
| WO | WO2012/084202 A2 | | 6/2012 | |
| WO | WO2013/055293 A1 | | 4/2013 | |

OTHER PUBLICATIONS

Chinese Office Action dated May 8, 2019 issued in connection with Chinese Application No. 201680058890.9.
Office Action dated May 12, 2020 in connection with related Brazilian Patent Appl. No. BR112018005496-8.

* cited by examiner

STENT GRAFT

The invention relates to a stent graft consisting of a stent comprising a plurality of ring segments arranged side by side and interconnected by connecting webs, and a membrane, said membrane covering the entire outer side of the stent, being wrapped inwards around the ends of the stent and being fixed between loops of the ring segments and the connecting webs between adjoining ring segments. Moreover, the invention also relates to the use of such a stent graft with a view to treating vascular malformations and a method for the manufacture of such stent grafts.

Stent grafts of this type are used in blood vessels, e.g. to give support to abnormally narrowed, dilated or damaged blood vessels. The combination of stent and membrane is also used to treat extended, vascular sections in need of treatment and requiring an implant of greater length and, above all, flexibility. In particular, stent grafts are employed to bridge vascular malformations, for example to isolate aneurysms from the blood circulation. Balloon catheters are usually used for the implantation of such stent grafts State-of-the-art stent grafts consisting of two stents and a flexible membrane, such as Teflon, are known to be used for this task. Such a stent graft is described in publication EP 2 151 217 A1. The disclosed stent graft consists of an inner stent and an outer stent arranged coaxially around this first one, between which a flexible, expandable membrane is arranged. The end areas of the stents with the membrane located in between are welded together.

Publication EP 1 266 635 A2 discloses a stent graft comprising a cylindrical stent and a cylindrical membrane, which are, for example, connected to each other by seams or hooks. In addition or alternatively, the connection can be secured by a slight overlap of stent and membrane.

WO 2009/035679 A1 discloses a stent graft being provided with a continuous inner liner made of polyester or ePTFE. A stent is arranged at one area of this inner liner and encloses the inner liner coaxially. The areas of the inner liner adjacent to the stent are coated with a second layer made of polyester or ePTFE to increase the wall thickness of the implant in the area not supported by the stent. The end areas of the stent and the second layer are pushed against each other. If necessary, additional reinforcing material, e.g. ePTFE, can be applied to the outside of the stent graft components, especially at the transitions between the stent and the second layer.

Of the above-mentioned stent grafts providing for a membrane connecting to a stent, only the stent shown in EP 1 266 635 A2 connects exactly one stent with exactly one membrane. The other prior-art solutions always require another stent or another membrane, which is arranged coaxially around the first stent or membrane for reinforcement purposes.

The solution according to EP 1 266 635 A2 uses hooks or threads and/or alternatively an overlap of both components for the connection between stent and membrane. In this respect, the durability of the hooks and threads, which are exposed to high frictional forces within the blood vessel, is always problematic. Moreover, there is also the risk of tissue irritation or injury as a result of hooks sticking out or edges protruding between the stent and membrane.

Stent grafts are also described in WO 2012/084202 A1 and WO 01/66035 A2. In this case, the membrane is fixed at the peripheral ring segments, which means that the expansion of the stent during placement can impair the fixation of the membrane on the stent.

It is, therefore, the objective of the present invention to propose a stent graft that simply and durably connects the stent and membrane, consumes very little vascular lumen and does not cause tissue irritation or injury. In particular, the connection between the membrane and the stent should not be provided at the ring segments in order to ensure a secure fixation of the membrane.

This objective is achieved by the invention proposing a stent graft of the kind first mentioned above, in which the membrane is fixed between at least two loops of the second ring segments, seen from the ends of the stent, and the connecting webs extending to the adjacent terminal ring segments.

The loops or individual loops of the second ring segments can be extended in the direction of the adjacent terminal ring segment.

The stent graft proposed by the invention consists of a plurality of meandering ring segments interconnected by connecting webs. These connecting webs and ring segments correspond to the ring segments of conventional stents, as they are often suggested and used. Only the ring segments located adjacent to the terminal ring segments, i.e. the second ring segments when viewed from the ends of the stent, can be designed and modified in accordance with the invention.

By peripheral ring segments, ring segments are to be understood that are arranged at the end of the stent, that is, which limit the stent at its ends. Like the other ring segments, they have a meandering web pattern and are connected to the adjacent ring segments (the second ring segments) by means of connecting webs.

A meandering web run of the ring segments is understood to mean both a wavelike web run and a zigzag-shaped web run. Wavelike and zigzag-shaped web runs and ring segments are commonly used for vascular stents in order to accommodate the dilatation that occurs during expansion.

Customary connecting webs extend between the ring segments. These connecting webs can have a straight configuration and, in this case, connect either the valleys (inner arches) of adjacent ring segments with each other or alternatively the arch of a loop of a ring segment with the valley of a loop of the adjacent ring segment. Connecting webs can also have a curved shape, for example be S-shaped or spirally wound or coiled. The arrangement and shape serve to compensate at least partially for the length contraction that occurs during the expansion of the stent.

Arches and valleys of the ring segments are the peaks or reversal points of the loops of the ring segments resulting from the meandering configuration of the ring segments on the one hand and the depressions on the other. Each arch has two neighboring valleys, each valley has two neighboring arches. A valley represents an inner arch, the peak is an outer arch.

The stent graft proposed by the invention consists of a stent comprising a plurality of ring segments arranged next to each other and joined with each other by means of connecting webs, said ring segments having a meandering shape or configuration. The stent is covered on its entire outer side by a membrane which is wrapped inwards around the ends of the stent and is fixed on the inner side—in the lumen—of the stent between loops of ring segments and adjacent connecting webs in such a way that connecting webs are located on one side of the membrane and loops of the ring segments on the other side of the membrane.

The membrane is preferably fixed behind each or every second loop of the second ring segment.

As provided by the invention, the membrane is fixed at both ends of the stent between the loops of the second ring segment, as viewed from the ends, and the connecting webs to the terminal ring segment. The terminal ring segment is thus surrounded by the membrane on both sides.

To make sure in the stent graft proposed by the present invention that the fixation is appropriately secured both during and after expansion, at least one of the loops of each of the second ring segments is preferably elongated in the direction of the respective stent end, especially each of the loops behind which the membrane is fixed.

In order to enable such a kind of fixation of the membrane, the connecting webs attaching to the terminal ring segment of the stent terminate in a loop valley in the second ring segment. This allows the membrane to be pushed between the connecting webs and the arches of the ring segments and held in place. The connecting webs in this area are preferably straight and, starting out from the arches of the terminal ring segments that point inwards into the stent, extend into the valleys of the second ring segments. Alternatively, the connecting webs may also connect the valleys of the terminal ring segments with the valleys of the second ring segments.

To improve the retention of the membrane in the region of the second ring segment, at least one of the loops is extended into the direction of the end of the stent. In particular, the loops of the second ring segment that point to the outside of the stent are elongated in an alternate fashion. In this case, the elongated loops of the second ring segments may be longer by 50 to 150% compared to the shorter loops of the second ring segments.

During the expansion of the stent, this lengthening of the loops causes the longer loops to undergo a relatively minor shortening in relation to their length, while the length reduction of the shorter loops is rather significant. This means that the retention of the membrane under the longer loops is essentially effective.

Alternatively or in addition, the loops of the second ring segment pointing to the outside of the stent may be provided with blind webs that point towards the stent outside. These blind webs do not serve to connect the ring segment with the neighboring ring segment; they end freely and can thus contribute to the retention of the membrane. Such a blind web may extend the loop from which arch it originates by 50 to 100%. In the course of this, the blind webs may project into the valleys of the terminal ring segments. The blind webs are to be considered a form of loop extension, behind which the membrane can be fixed.

The stent graft proposed by the present invention will as a rule comprise a stent that can be expanded by means of a balloon catheter, for example, a stent made of medically acceptable steel. Alternatively, it is also possible to use variants providing for the stent to be of self-expanding design, e. g, by using a shape-memory alloy such as nitinol.

The membrane, usually consisting of a film or a tube, can consist of any desired material as it is customarily employed and approved in the medical field. However, PTFE and polyester are particularly suitable, Especially preferred is a membrane made of ePTFE. The membrane can also be functionally coated, for instance with anti-inflammatory, proliferation-inhibiting or therapeutic substances such as rapamycin, paclitaxel or heparin, for example. The membrane is preferably tubular in shape and has the required elongation capability to go along with the stent expansion.

The stent grafts proposed in accordance with the invention are primarily used for the treatment of vascular malformations. This may involve the closure of diverging or branching vessels, but also the occlusion of aneurysms or arteriovenous shunts.

Moreover, it is also possible to provide embodiments in which the inventive stent graft comprises two stent units that serve to clamp an intermediate tubular membrane into a vessel. In this case, the stent has the clamp connection for the fixation of the membrane only at one end; the other end of the tubular membrane being connected to the second stent. Such a stent graft can be implanted into extensively damaged vessels, for example after obliteration of the epithelial cell layer of a blood vessel.

The invention also relates to a method for the manufacture of the inventive stent grafts involving the following steps:

Provision of a stent with interconnected ring segments having a meandering configuration;

Inward bending of at least one loop of a ring segment that is located adjacent to a peripheral ring segment;

Applying a tubular film to the stent;

Wrapping the tubular film around at least one peripheral ring segment so that the end of the tubular film extends into the lumen of the stent;

Sliding the end of the tubular film underneath the ring segment loops bent inwards;

Fixing the end of the tubular film to the stent by bending back the loops bent in wards.

Preferably, the tubular film is wrapped around and fixed at both ends of the stent. Preferably, the fixation takes place under several loops of the ring segments located adjacent to the peripheral ring segments. In particular, every second or each loop of the respective ring segment is used for fixation, i.e. every second or each loop of the respective ring segment is bent open and bent back again after the tubular film has been pushed in place.

The stent covered with the tubular film can subsequently be crimped onto a balloon in the usual way and transferred to the placement site with the help of a balloon catheter.

It goes without saying that the film that is used to manufacture the stent graft must have sufficient extensibility to be appropriately widened without tearing during the placement of the stent. This is achieved, for example, when using ePTFE as material for the film or the tube.

Figure 2:
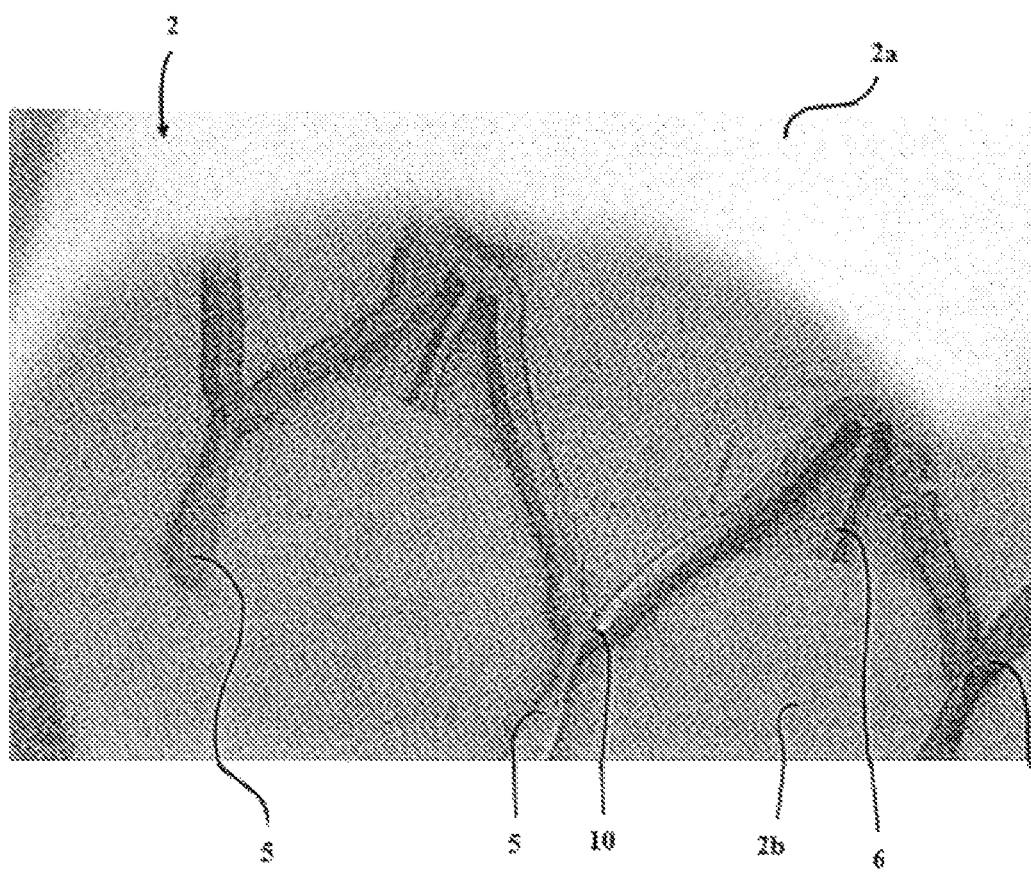
Figure 1A:
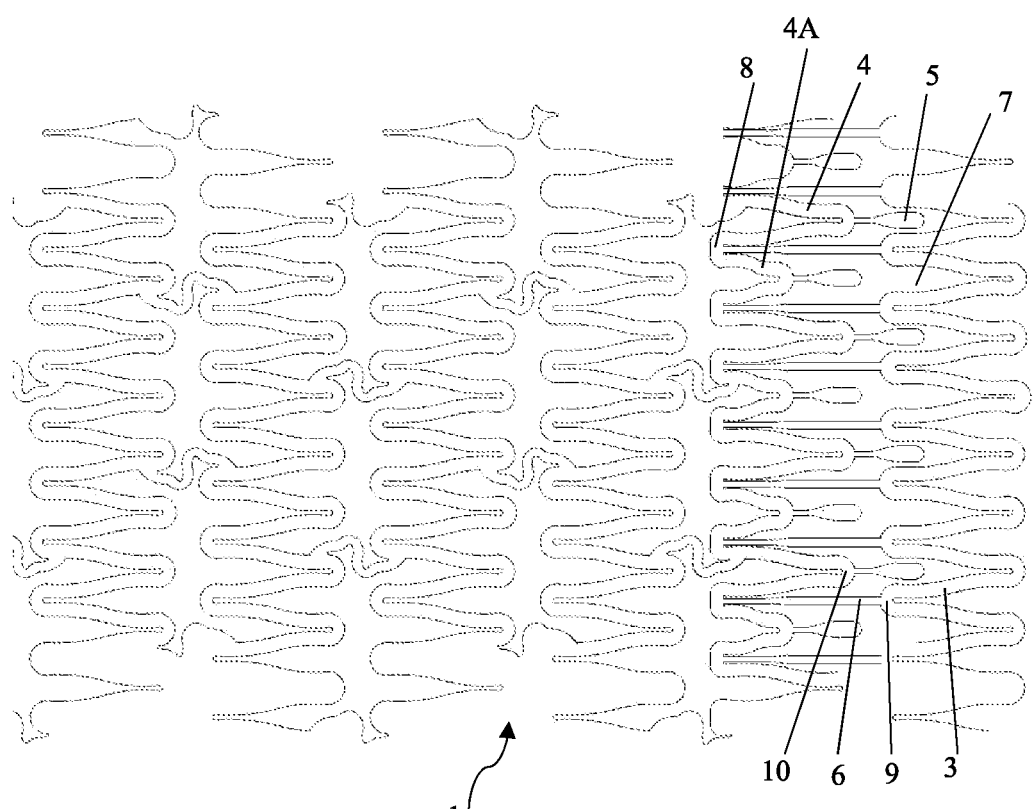
Figure 3:
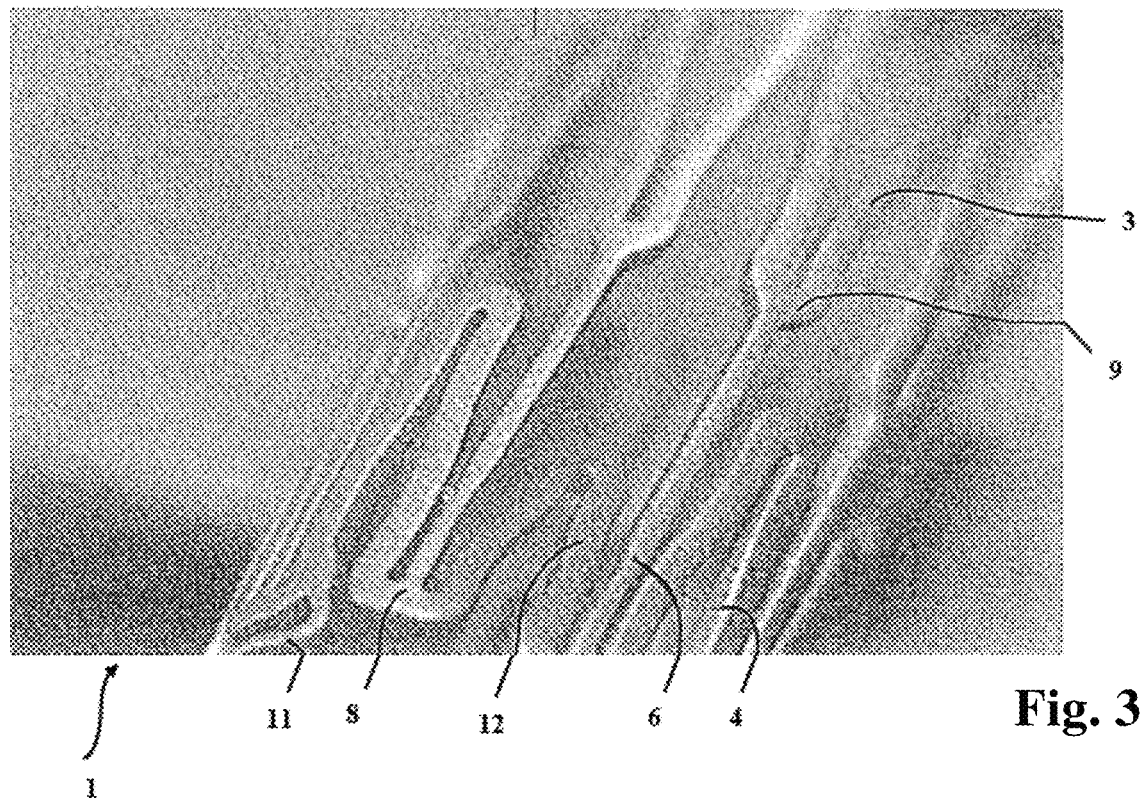
Figure 4:
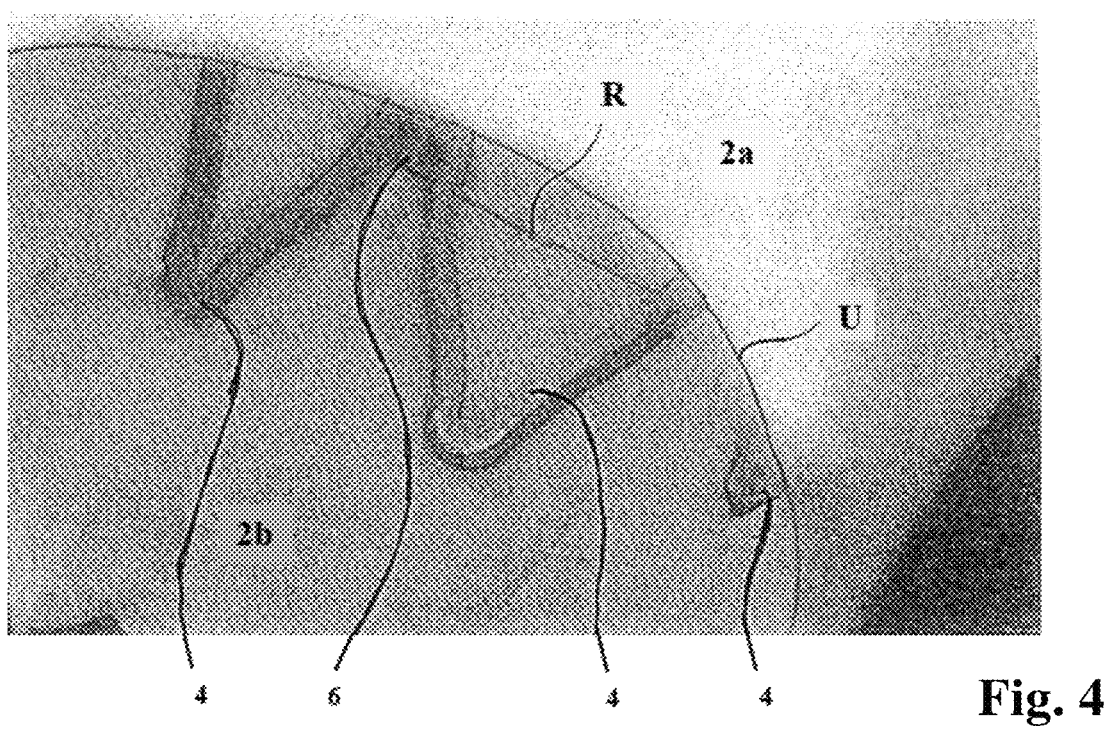

Further elucidation of the application is provided through the enclosed figures of preferred embodiments, where FIG. 1: illustrates a stent design that can be employed for a stent graft proposed by the invention;

FIG. 1A: illustrates an alternative stent design that can be employed for a stent graft proposed by the invention;

FIG. 2: shows a photo of the stent as per FIG. 1 provided with a tubular film fixed in accordance with the invention;

FIG. 3: shows the photo of a stent design with loop bent inwards in the second ring segment; and FIG. 4: shows a photo of the stent illustrated in FIG. 3 with tube secured in position.

FIG. 1 shows a stent 1 designed to comprise meandering ring segments 3 and 4 in a planar representation. The ring segment 3 is a peripheral or terminal segment, i.e. it forms the end of the stent 1. The neighboring ring segment 4 is connected via straight webs 6 to the peripheral ring segment 3, whereby webs 6 extend from the outer arches 9 of the loops of the peripheral ring segment 3 into the inner arches 8 of the adjacent ring segment 4.

The loops of the second ring segment 4 are provided with blind webs 5 arranged on their outer arches 10, said blind webs do not establish any connection to the neighboring ring segment 3, they terminate unconnected. These blind webs 5 are used to extend the loops of the second ring segment 4;

upon the expansion of stent 1, said loops elongate and in this elongated state are no longer capable of securely holding a cover in place that is fixed behind them. The blind webs 5 thus increase the contact with the cover and in this way improve its retention.

In the case illustrated, the blind webs 5 extend into the inner arches 7 of the peripheral ring segment 3. Their length amounts to approx. 50% of the loop length of the second ring segment 4 when the stent is in non-expanded state.

FIG. 1A shows a stent of an alternative design wherein there are alternating ring segments 4 and 4A, the other lead lines 3, 5, 6, 7, 8, 9, and 10 point to features corresponding to those of FIG. 1.

In FIG. 2, a photo of the stent 1 illustrated in FIG. 1 is shown with cover 2 fixed to it, wherein the outer side of cover 2 is marked with reference numeral 2a while the end of cover 2 wrapped around the end of the stent is marked with 2b. The photo was taken from the front side of the stent 1 into the lumen.

In the case illustrated, cover 2 is a tubular film made of ePTFE, which is pulled over the stent, is guided with its end 2b around the end of the stent and is clamped between the outer arches 10 with blind webs 5 of the second ring segment 4 on the one hand and the connecting webs 6 arranged between ring segments 3 and 4 on the other hand, Caused by the expansion of stent 1, the loops of the second ring segment 4 have been widened considerably.

Basically, the tubular film 2 is wrapped around both ends of stent 1 and fixed in the manner described hereinbefore. However, applications are conceivable where a fixation at only one end of the stent is sufficient.

By means of a photo taken along the stent axis, FIG. 3 illustrates the way in which cover 2 is fixed in the lumen of stent 1. The end of the stent is situated at the upper edge. As is also evident from FIG. 1, the second ring segment 4 is connected via connecting webs 6 with the outer arches 9 of the first ring segment 3. The ring segments forming the subsequent stent structure are connected with each other via S-shaped webs 11. One of the loops of ring segment 4, marked here with reference numeral 12, is bent inwards. This facilitates pushing the end of a cover underneath, in particular a tubular film 2, which is subsequently fixed by bending back the bent loop 12. In actual practice however, more than only one loop is bent over for fixation purposes; this is preferably the case with each loop or every other loop.

In FIG. 4, the stent of FIG. 3 is illustrated on the basis of a photo similar to FIG. 2 with a tubular film 2 fixed to it, said film being secured between the loops of the ring segment 4, which have meanwhile been bent back, and connecting webs 6. Reference numeral 2a designates the outer portion of tubular film 2, while numeral 2b refers to the wrapped around portion. The connecting web 6 is just visible here. U designates the cover wrapping edge of tubular film 2/2a, whereas R refers to the edge of the folded around and fixed part 2b.

It is to be understood that the embodiments described hereinbefore represent examples only, and that the individual features of these exemplary embodiments can occur in any conceivable combination in the stent grafts proposed by the invention.

The invention claimed is:

1. A stent graft consisting of a stent (1) and at least one membrane (2), the stent having two stent ends, an outer side and an inner side of the stent, the stent comprising a plurality of ring segments (3, 4), each of the ring segments having a meandering configuration thus creating loops with arches and valleys, the ring segments being arranged side by side and being connected with each other by connecting webs (6), with a terminal ring segment (3) being located at each end of the stent and a second ring segment (4) being located adjacent to the terminal ring segment, loops of the second ring segments alternately differ in length resulting in short loops (4A) and long loops (4), the at least one membrane (2) covering the entire outer side of the stent (1), and being folded inwards around at least one end of the stent and fixed between loops of the second ring segment (4) and connecting webs (6) that join the second ring (4) and the terminal ring segment (3), wherein the membrane (2) is fixed by clamping the membrane (2) between at least two loops of the second ring segment (4) and the connecting webs (6) connecting the second ring segment (4) and the adjacent terminal ring segment (3).

2. Stent graft according to claim 1, characterized in that the terminal ring segments (3) have outer arches (9) and are connected to the adjacent ring segments (4) by straight connecting webs (6), said straight connecting webs (6) leading from the terminal ring segments' (3) outer arches (9) that point to the interior of the stent into the valleys or inner arches (8) of the second ring segments (4).

3. A stent graft consisting of a stent (1) and at least one membrane (2), the stent having two stent ends, an outer side and an inner side of the stent, the stent comprising a plurality of ring segments (3, 4), each of the ring segments having a meandering configuration thus creating loops with arches and valleys, the ring segments being arranged side by side and being connected with each other by connecting webs (6), with a terminal ring segment (3) being located at each end of the stent and a second ring segment (4) being located adjacent to the terminal ring segment, loops of the second ring segments (4) point to the outside of the stent and alternately differ in length resulting in short loops (4A) and long loops (4), the at least one membrane (2) covering the entire outer side of the stent (1), and being folded inwards around at least one end of the stent and fixed between loops of the second ring segment (4) and connecting webs (6) that join the second ring (4) and the terminal ring segment (3), wherein the membrane (2) is fixed by clamping the membrane (2) between at least two loops of the second ring segment (4) and the connecting webs (6) connecting the second ring segment (4) and the adjacent terminal ring segment (3).

4. Stent graft according to claim 3, characterized in that a length ratio of the short to the long loops of the second ring segments amounts to 1:2 to 2:3.

5. Stent graft according to claim 1, characterized in that second ring segment (4) have outward-facing arches (10) extended toward the outside of the stent by blind webs (5).

6. Stent graft according to claim 5, characterized in that the blind webs (5) have a length which amounts to between 50 and 100% of the length of the loops (4) provided with blind webs (5).

7. Stent graft according to claim 5, characterized in that the terminal ring segments (3) have valleys (7) and blind webs (5) project into the valleys (7) of the terminal ring segments (3).

8. Stent graft according claim 1, characterized in that the at least one membrane (2) is in the form of a tube.

9. Stent graft according to claim 1, characterized in that the at least one membrane (2) consists of ePTFE tube.

10. Stent graft according to claim 1, characterized in that the stent (1) is a balloon-expandable stent.

11. An assembly comprising a stent graft according to claim 10 and a balloon catheter comprising a balloon, wherein the stent graft is crimped onto the balloon of the balloon catheter.

12. Stent graft according to claim 1 in which the stent is self-expanding and made of a shape-memory alloy.

13. Method for manufacturing a stent graft according to claim 1 involving the steps of
providing a stent (1) with interconnected ring segments (3, 4) having a meandering configuration wherein the ring segments (3, 4) comprise a plurality of loops;
bending inward of at least one loop (12) of a ring segment (4) that is located adjacent to a peripheral ring segment (3) to obtain an inward facing loop;
fitting a tubular membrane (2) onto the stent (1);
wrapping the tubular membrane (2) around at least one peripheral ring segment (3) so that the end of the tubular membrane (2) extends into the inner side of the stent (1);
pushing the end (2b) of the tubular membrane (2) under the inward facing loops (12) of the ring segment (4); and
fixing the end (2b) of the tubular membrane (2) to the stent (1) by bending back the loops (12) bent inwards.

14. Method according to claim 13, characterized in that the tubular membrane (2) is wrapped around and fixed at both ends of the stent.

15. Method according to claim 14, characterized in that the fixation is effected under several loops (12) of the ring segments (4) located adjacent to respective peripheral ring segments (3).

16. Method according to claim 15, characterized in that the fixation is effected under each or every second loop (12) of the ring segments (4) located adjacent to respective peripheral ring segments (3).

17. Method according to claim 13, characterized in that the tubular membrane (2) of the stent graft is crimped onto a balloon.

18. Stent graft according to claim 12, wherein the shape memory alloy is nitinol.

* * * * *